United States Patent [19]

Fleenor et al.

[11] Patent Number: 5,707,379
[45] Date of Patent: Jan. 13, 1998

[54] METHOD AND APPARATUS FOR INTRACORPOREAL SUTURING

[75] Inventors: Richard P. Fleenor, Englewood; Robert L. Bromley, Arvada, both of Colo.

[73] Assignee: Coral Medical, Englewood, Colo.

[21] Appl. No.: 546,581

[22] Filed: Oct. 20, 1995

[51] Int. Cl.⁶ .................................................. A61B 17/04
[52] U.S. Cl. ........................ 606/145; 606/144; 606/139
[58] Field of Search ................................ 606/145, 149, 606/148, 139, 147; 112/169

[56] References Cited

U.S. PATENT DOCUMENTS

| | | | |
|---|---|---|---|
| 4,109,658 | 8/1978 | Hughes | 128/340 |
| 4,557,265 | 12/1985 | Andersson | 128/340 |
| 5,304,185 | 4/1994 | Taylor | 606/147 |
| 5,308,353 | 5/1994 | Beurrier | 606/144 |
| 5,454,823 | 10/1995 | Richardson et al. | 606/148 |

*Primary Examiner*—Michael Buiz
*Assistant Examiner*—Tina T. D. Pham
*Attorney, Agent, or Firm*—Davis, Graham & Stubbs LLP

[57] ABSTRACT

A suturing device includes a rod partially covered by an elongate tube. A guide containing a one way slot is mounted to an end of the rod; a similar guide is mounted to the same end of the tube. The rod and tube may be rotated with respect to each other by manipulating an attached handle. A suturing needle with suture material attached may be fitted into a slot in one of the guides. Rotating the guides allows the needle to be passed between the needle guides, and the one way slot action allows the needle to be separated from one of the guides, so that the needle may passed around the device in an approximate circle. The device may be moved longitudinally as the needle is passed between the needle guides to form a series of stitches.

14 Claims, 6 Drawing Sheets

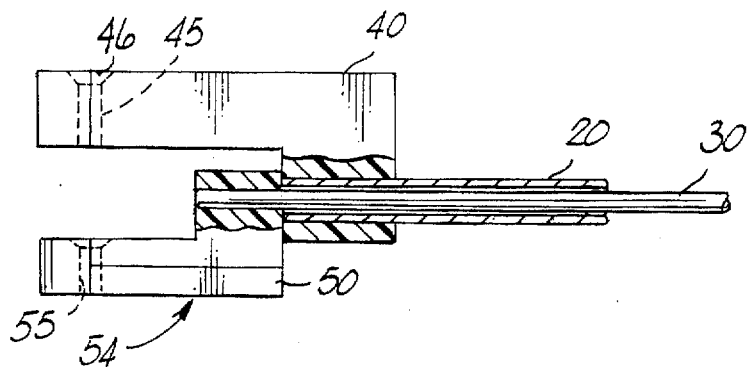
FIG. 2
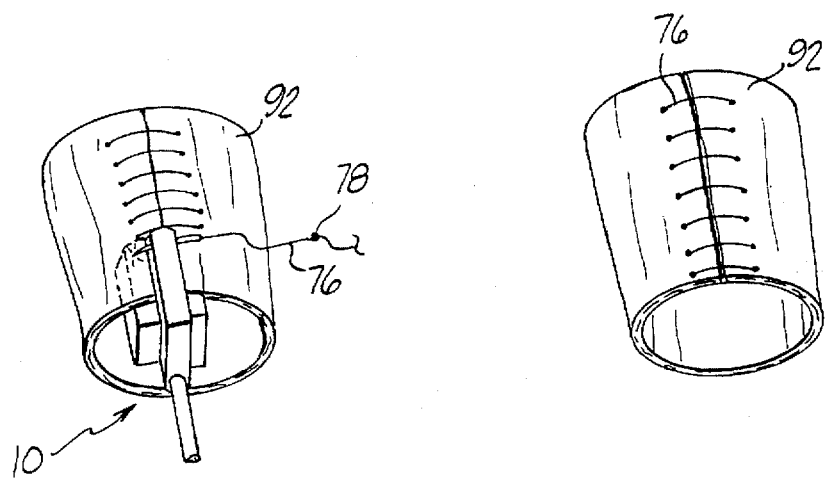
FIG. 4
FIG. 5
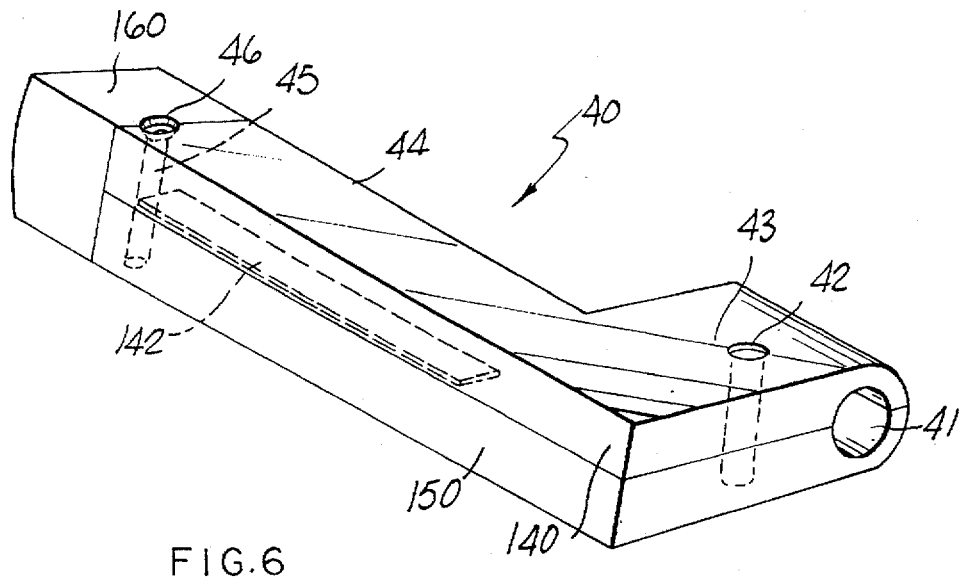
FIG. 6

METHOD AND APPARATUS FOR INTRACORPOREAL SUTURING

FIELD OF THE INVENTION

The present invention relates to the broad field of suturing, and more specifically to a device useful for intracorporeal suturing as occurs in laparoscopic surgery.

BACKGROUND OF THE INVENTION

Sutures are used in numerous medical procedures such as closing ruptured tissue or grafting tissue together. Traditionally, sutures have been placed by hand, with a surgeon repeatedly passing a thread-bearing needle through the tissue to be sutured. Although this is a tedious and time consuming task, satisfactory results may generally be obtained. However, the traditional suturing method cannot be used with surgical techniques that allow surgery to be performed inside of a patient's body by accessing the surgical site through an introducing tube or tubes, such as trocars and cannulae.

In these surgical techniques, the surgeon does not have direct visual or tactile access to the operation site; instead, the site is viewed through a laparoscope or endoscope or similar device, and the surgery is performed through specialized instruments inserted through the introducing tubes. In the following discussion, the term laparoscopy is meant to encompass any form of invasive surgery that is performed inside the body of a patient via introducing tubes, since the distinctions between the various types of invasive surgery are not germane to the present invention.

Laparoscopic surgery is often preferable to traditional open surgery because it is less invasive than traditional open surgery—the smaller wound created during the surgical procedure allows for a much more rapid recovery by the patient. The patient may thus have a shorter hospital stay or, in some cases, no hospital stay whatsoever.

Traditional manual surgical techniques cannot be used in laparoscopic surgery, since a surgeon cannot place his hands at the operation site. Still, it is necessary or desirable to place sutures in many different laparoscopic procedures. For example, in laparoscopic cholecystectomy, the cystic duct or artery can be ligated using suturing and knot tying techniques rather than the alternative technique of an automatic clip. Although laparoscopic staplers have been developed, laparoscopic sutures will still be needed for many purposes such as closing defects in a staple line, placing purse-string sutures for end-to-end stapling, closing mesenteric defects, and ligating large blood vessels.

Several devices and techniques have been developed to fit through the narrow tubes used in laparoscopic suturing. The most basic devices are simple needle holders that use plier-like opposable jaws to grasp and manipulate a suturing needle. However, the small, curved needles used in laparoscopic surgery are difficult to grasp, and may easily slip from a needle holder, causing unnecessary tissue damage to the patient, and a consequently longer recovery period. Also, it is a slow and difficult process to manipulate the suturing needle through an introducing tube, which allows for a prolonged time for a surgeon to make an error, such as inadvertently allowing the needle to slip from the needle holder. Attempts have been made to improve upon the plier-like needle drivers, such as in U.S. Pat. No. 5,376,096 issued Dec. 27, 1994 to Foster. However, as with plier-like needle drivers, the Foster device does not firmly connect the needle driver to the needle, so that the needle may still be misdirected or even lost in the body of the patient.

More sophisticated suturing devices have been developed for laparoscopic type surgery. For instance, U.S. Pat. No. 5,364,408 issued Nov. 15, 1994 to Gordon discloses a device where two needles extend from opposite sides of the device, and may be pushed through surrounding tissue and then be recaptured by the device. While this device may be useful for making a single loop suture, its inability to make sutures of more than one loop limits its versatility. U.S. Pat. No. 5,403,328 issued Apr. 4, 1995 to Shallman discloses a device with a needle pivotally attached to an elongate tube that may be inserted into the body of a patient. A suture may be placed by pivoting the needle away from the device and retracting the device. However, the device makes no provision for retracing the needle adjacent to its initial pass, hence it is only useful to place one stitch and may not be used to place a series of stitches, which is commonly required in laparascopic suturing. A similar device is disclosed in U.S. Pat. No. 5,397,325 issued Mar. 14, 1995 to Della Badia et al. U.S. Pat. No. 5,437,681 issued Aug. 1, 1995 to Meade et al. discloses a device that allows for a series of stitches to be placed in the body of a patient. That device is quite complicated, containing numerous springs, gears, cams, and pinions with their attendant manufacturing costs and the possibility of malfunction. Also, the Meade et al. device is positioned on only one side of the tissue to be sutured, which allows the tissue to be displaced by the penetrating action of the needle. Thus, there exists a need for a simple suturing device which may be used to place a suture of any desired length into a patient's body during a laparscopic or similar operation.

SUMMARY OF THE INVENTION

The present invention is a method and apparatus for suturing, with particular application to laparascopic surgery or similar surgical methods where surgical instruments are placed into the body of patient through introducing tubes. The suture may be a standard spiral stitch or may have a different stitch pattern if desired.

A device embodying the present invention includes a rod and a concentric tube placed around a segment of the rod. The rod and tube may be rotated in relation to each other in either direction. The rod may be rotated by manipulating a handle located at the proximal end of the device. The handle resembles that of scissors, in that it consists of two finger-ring equipped lever arms, that are hinged together. One lever arm is attached to a screw, and the other end of the screw is attached to the rod. Moving the lever arms pushes or pulls the screw. A handle body contains protrusions that mesh with the screw thread, so that the screw rotates as it is pushed or pulled. The rod is coupled to the screw with a tongue and groove connection that allows longitudinal motion therebetween, but causes the rod and screw to rotate together. The tube is attached to the handle body, so the rotation of the screw causes the rod to rotate relative to the tube.

The distal end of the device includes a first needle guide attached to the tube and a second needle guide attached to the rod. The needle guides extend radially out from the rod and tube and project distal to the rod and tube. Rotating the rod and tube in relation to each other rotates the needle guides, whose rotational path defines a circumference around the axis of rod and tube. Each needle guide contains a one way needle slot, that allows the needle to move through the slot when the needle travels through the slot in one direction. However, the needle binds in the slot when force is applied urging the needle in the opposite direction.

A suturing needle with a pointed end and suturing thread attached to the opposite end is placed through one of the guides (assume the first guide for the following description) before the device is introduced into the body of patient. The device is then positioned so that the two guides are on opposite sides of a tissue surface that is to be sutured. The second guide is positioned against the tissue. The first guide is then rotated so that the needle passes through the tissue and into the slot of the second guide. The second guide may then be rotated, and the one way directional slots causes the needle to bind in the second slot and to move along with the second guide. Thus, the needle is passed through the tissue surface to be sutured. The first needle guide may be rotated in the opposite direction from its initial rotation, until it abuts the tissue. The first needle guide will then abut the tissue on the opposite end of the circumferential arc defined by the rotational path of the first needle guide, compared to the point at which the needle was passed from the first needle guide to the second. The second needle guide may be further rotated so that the needle is passed through the tissue again, back to the first needle guide. The process can be repeated a number of times to achieve a desired suture length. Along with passing the needle through the tissue between the needle guides, the device may also be moved longitudinally or radially to form, for example, a spiral suture or a mattress suture.

To perform laparascopic suturing, the distal end of the device is inserted into an introducing tube, which extends from outside of the patient's body to the operation site within the patient's body. The handle of the device is left outside of the tube and outside of the patient's body, so that a surgeon may manipulate the handle and thus the needle guides. Once the suture is placed, the suture material may be severed and knotted by any of the means known in the art. Finally, the suturing device is withdrawn from the introducing tube.

The one way needle slot action may be achieved by several methods. In a preferred embodiment, a resilient shim protrudes into the needle slot. The needle may be pushed through the slot, and will deflect the shim into a receiving groove in the needle guide. As the needle motion is continued and a portion of the needle passes the shim, the needle motion cannot be reversed, because the needle blocks the path the shim would have to take to assume its initial position.

The present invention may be dimensioned to be inserted through introducing tubes of various sizes, allowing for its use in laparoscopic surgery. Because the invention positively grips the suturing needle and supports the surrounding tissue, it may be used without the assistance of any other device, such as clamps, and eliminates the possibility of losing the needle within a patient's body. Also, tissue damage resulting from passing a needle through unsupported tissue is reduced.

The device may be operated with one hand, allowing the surgeon to use his other hand to perform other tasks. The present invention achieves the above advantages even though it comprises substantially fewer components and is of a simpler design than prior art suturing devices.

BRIEF DESCRIPTION OF THE DRAWINGS

FIG. 2 is a partially sectional side view of the distal section of FIG. 1, shown in greater detail.

FIG. 4 is a perspective view of the device of FIG. 1 placing a suture in a curved surface.

FIG. 5 is a perspective view of a spiral stitch suture placed by the device of FIG. 1.

FIG. 6 is a perspective view of a needle guide of FIG. 1 with portions cut away.

DETAILED DESCRIPTION OF THE INVENTION

Figure 1:
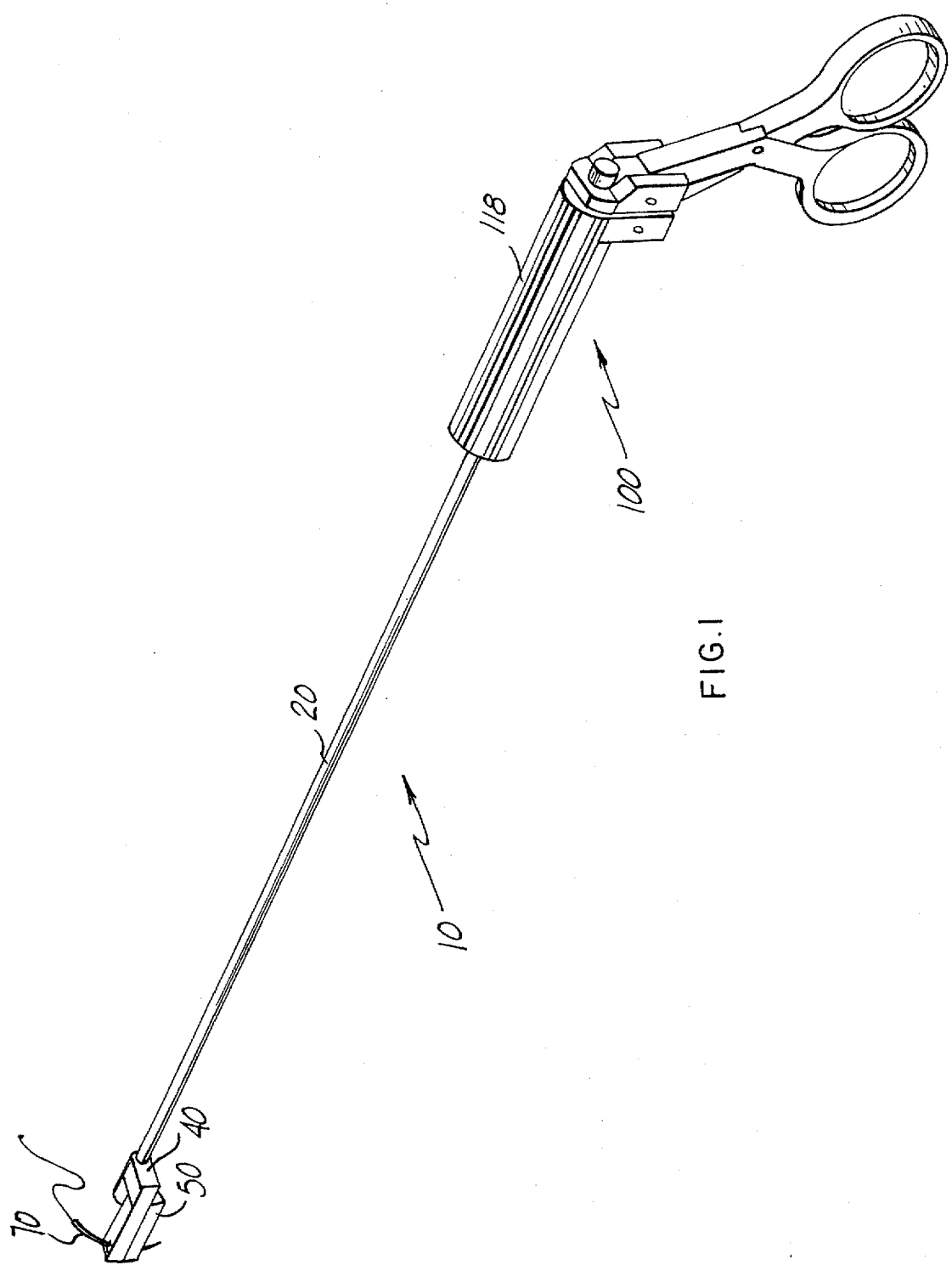
FIG. 1 shows a perspective view of a device in accordance with the present invention.

With reference to FIG. 2, the present invention 10 includes an elongated tube 20 having a proximal end and a distal end. A rod 30 is placed through the inside the tube 20 and extends beyond each end on the tube 20. Longitudinal, radial, and tangential directions are defined with reference to the common axis of the rod 30 and tube 20. A first needle guide 40 is attached to the distal end of the tube 20 and a second needle guide 50 is attached to the distal section of the rod 30 that extends distal to the tube 20. The distal end of the tube 20 fits into a hole 41 in the first needle guide 40, and a tensioning device such as a screw 42 (see FIG. 6) in the first needle guide 40 allows the, first needle guide 40 to be securely attached to the tube 20.

The first needle guide 40 is "L" shaped, so that the hole 41 penetrates the short leg 43 of the needle guide 40 near the portion of the short leg 43 opposite the portion that joins the long leg 44 of the needle guide 40, and the hole 41 axis is parallel to the axis of the long leg 44 of the needle guide 40 (see FIG. 6). The long leg 44 of the needle guide 40 is thus radially disposed away from the rod 30, and is parallel thereto. The distal end of the long leg 44 extends distal to the tube 20 and the rod 30.

The long leg 44 of the needle guide 40 is tangentially punctured by a one way needle slot 45 in the portion of the leg 44 that extends distal to the rod 30 and tube 20. The one way needle slot 45 allows a needle 70 to pass through the slot 45 in only one direction. Attempting to move the needle 70 through the one way slot 45 in the opposite direction will cause the needle 70 to bind in the one way slot 45. The structure of the slot 45 that causes its one way operation is described below.

A second needle guide 50 is attached to the distal end of the rod 30 that extends beyond the distal end of the tube 20. The second needle guide 50 is substantially similar to the first needle guide 40. It has the same L shape, but the long leg 54 of the L is somewhat shorter so that the distal end of the long leg 54 extends to the same longitudinal position as does the first needle guide 40. A one way slot 55 is located in the second needle guide 50 in a corresponding position as the first needle slot 45 is located in the first needle guide 40, so that the needle slots 45, 55 are the same longitudinal distance beyond the distal end of the rod 30 and the same radial distance away from the axis of the rod 30. The one way directional action 45, 55 of the slots 45, 55 is the same for both slots.

The rod 30 and the tube 20 may be rotated with respect to each other. This rotating may be accomplished by the user of the device 10 by manipulating a handle 100 attached to the proximal ends of the rod 30 and the tube 20. The structure of the handle 100 is described below. Since the tube 20 and rod 30 are rigid, the distal end of the device 10 may be positioned longitudinally or radially by the manipulating proximal end of the device 10.

Figure 3A:
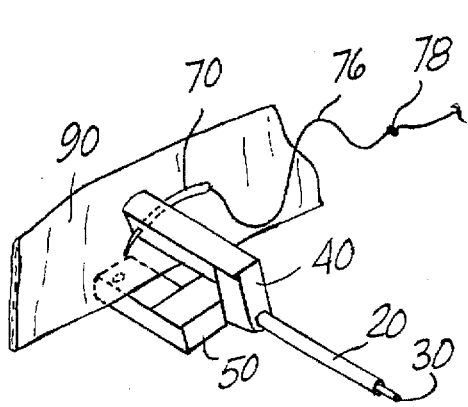
FIGS. 3A to 3F are views of the device of FIG. 1 placing a suture.

To use the device 10 to place a suture, a needle 70 is first placed in one of the needle guides 40, 50. The needle 70 is preferably curved and has a sharp end 71 and an opposite end to which suture material 76 is attached. In the following description of the operation of the device 10 to place a suture, assume that the needle 70 is first positioned in the needle slot 45 in the first needle guide 40, so that the both ends of the needle 70 extend beyond the slot 45 (see FIG. 3A). The needle 70 may be placed through the slot 45 before the device 10 is inserted into the body of the patient.

The second needle guide 50 is initially positioned away from the first needle guide 40 so that a space exists between the two guides 40, 50. The device 10 is positioned so that body tissue 90 to be sutured is in the space between the needle guides 40, 50. The first needle guide 40 is rotated so that it approaches the second needle guide 50. Since the sharp point 71 of the needle 70 extends beyond the needle guide 40, the sharp point 71 reaches the second needle guide 50 before the first needle guide 40 reaches the tissue 90. Because the needle slots 45, 55 are aligned, continued rotating of the needle guide 40 causes the needle 70 to pass from the slot 45 in the first needle guide 40 into the slot 55 in the second needle guide 50 (see FIG. 3B). When the needle 70 has been pushed through the slot 55 in the second needle guide 50 so that the needle 70 fully extends through the slot 55, the rotation of the first needle guide 40 is halted.

Figure 3B:
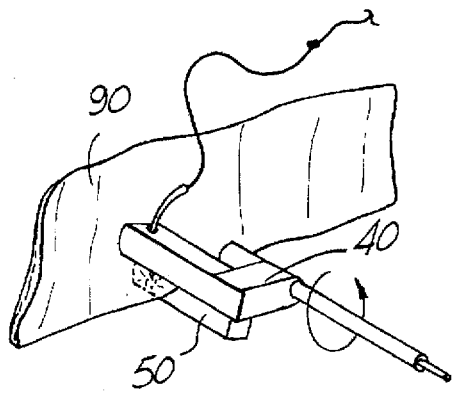
Figure 3C:
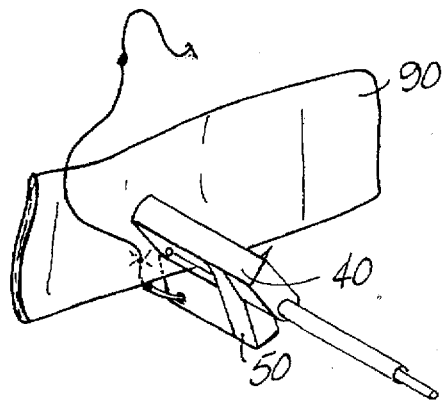

The second needle guide 50 is then rotated, continuing in the same tangential direction as the first needle guide 40 was initially rotated (see FIGS. 3B, 3C). The one way slots of the two guides 40, 50 are aligned in the same tangential direction, allowing the needle 70 to pass through the second needle guide 50 slot. When the second needle guide 50 is rotated, the second needle guide slot 55 grips the needle 70 so that rotation of the second needle guide 50 pulls the needle 70 along with the guide 50. This occurs because if the second needle guide 50 were to move over the needle 70 without gripping the needle 70, the relative motion between the needle 70 and the needle guide 50 would be opposite the direction of motion when the needle 70 is first passed through the second needle guide 50. The one way slot design prevents this motion.

Figure 3D:
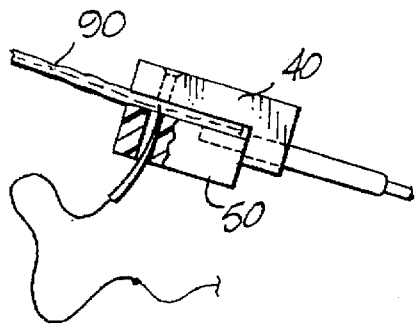
Figure 3E:
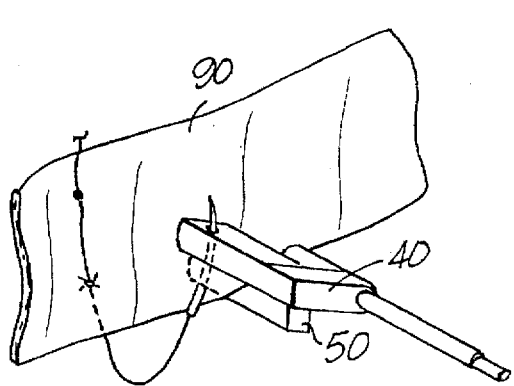
Figure 3F:
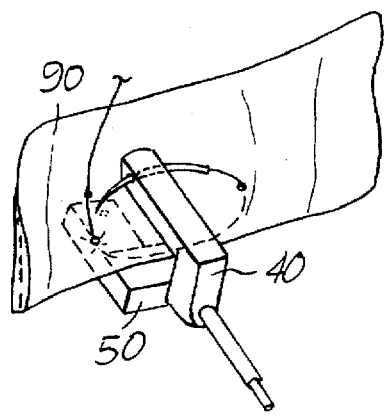

It can thus be appreciated that the two needle guides 40, 50 allow the needle 70 to be passed through tissue 90 to be sutured without either of the needle guides 40, 50 crossing that tissue 90. The needle 70 can then be passed back from the second needle guide 50 to the first needle guide 40, again through the surface of the tissue 90 to be sutured. The second needle guide 50 is further rotated in the same tangential direction, and the first needle guide 40 is rotated in the reverse tangential direction (see FIGS. 3D, 3E). Eventually, the needle 70 is rotated far enough so that the sharp point 71 of the needle 70 passes through the slot 45 in the first needle guide 40, in the direction of the one way slot 45 that allows for the passage of the needle 70. The rotation of the second needle guide 50 may be halted, and the first needle 40 may then be rotated in its original direction. Rotation in this direction will cause the first needle guide slot 45 to grip the needle 70, thus the needle 70 will be transferred back to the first needle guide 40. The rotation of the first needle guide 40 may be continued, and the second needle guide 50 may rotated in the reverse direction, so that the needle guides 40, 50 assume the position they were in before the needle 70 was passed from the first needle guide 40 to the second needle guide 50 (see FIG. 3F).

As shown in FIGS. 3A–3F, the suture material 76 attached to the end of the needle 70 is pulled along with the needle 70, so that a loop in the suture material 76 is formed as the needle 70 travels around circumference of the device 10. Preferably, the end of the suture material 76 opposite the needle 70 is terminated by a knot or a bead 78 to prevent the free end of the suture material 76 from being pulled through the tissue 90.

FIGS. 3A–3F show the device 10 passing the needle 70 through an essentially planar surface 90. The device 10 may also be used for suturing a curved surface 92, as shown in FIG. 4. The operation of the device 10 is then essentially the same as for suturing flat surfaces: the needle 70 is passed back and forth between the needle guides 40, 50 so that the needle 70 crosses the surface 92 to be sutured, but the guides 40, 50 do not. The needle guide on the concave side of the tissue 92 will not be rotated as much as the needle guide on the convex side of the tissue 92, since a greater portion of the circumference of the needle 70 path is on the convex side of the tissue 92. However, since the rod 30 may be completely rotated around the tube 20, the functioning of the device 10 is not impaired.

The use of the two needle guides 40, 50, one located on each surface of the tissue 90 (or 92), stabilizes the tissue when the needle 70 is passed through the tissue 90. The receiving needle guide, assume it is needle guide 50, may be placed adjacent to the tissue 90, so that the tissue 90 is not displaced by the needle 70 movement. When the needle 70 is passed through the tissue 90 and into the needle guide 50 so that the needle guide 50 may be rotated, along with the needle 70, away from the tissue 90, the other needle guide 40 may be repositioned so that it is adjacent to the opposite surface of the tissue 90. When the needle 70 is next passed between the needle guides 40, 50, the tissue 90 will again be stabilized. It can thus be appreciated that the device 10 may be used for suturing without the need for any supplemental devices, such as graspers. Also, the tissue 90 to be sutured will not be unnecessarily torn, as may occur if the tissue 90 is not stabilized at the time that it is punctured by the needle 70.

The device 10 may be moved longitudinally to place a series of stitches, such as a spiral stitch (see FIG. 5). After the needle 70 has been passed from one guide 40, 50 to the other, the user of the device 10 may push (or pull) on the proximal end of the device 10 to move the device 10 to a new position before the needle 70 is again passed between the guides 40, 50. After a sufficient number of passes are completed, the device 10 may be withdrawn from the body of the patient and the suture material 76 may be cut, knotted and tensioned using means known in the art. The device 10 may be used to form other stitch patterns, such as a mattress suture or a purse string suture, by appropriately positioning the needle guides 40, 50 before transferring the needle 70 between the guides 40, 50.

The length of a suture that can be made by the device 10 is limited by the distance that the needle slots 45, 55 extend beyond the proximal edge of the short leg 43 of needle guide 40. This is because it is only possible to position the needle guides 40, 50 on opposite sides of the tissue 90 to be sutured when the short leg 43 is proximal to the distal edge of the tissue 90 to be sutured. Otherwise, the needle guide holes 41, 51 that serve as the pivot points the needle guides 40, 50 would have to both be on the same side of the tissue 90, preventing the rotation of the needle guides 40, 50 more than 180°, which would not allow the needle 70 to be passed between the needle guides 40, 50. However, this is not a real impediment to the utility of the device 10, since the needle guides 40, 50 may be manufactured to any desired length.

With reference to FIG. 6, the operation of the one way slot 45 is now explained, it being understood that the one way slot 55 operates in the same manner. The needle guide 40 includes three constituent pieces: a first section 140, a second section 150, and an end cap 160. The first section 140 and second section 150 are both bisected sections of the L, taken along the axis of the long leg 44. When the first section 140 and the second section 150 abut against each other, the short leg 43 of the needle guide 40 is completely formed. The long leg 44 is formed up to the portion of the long leg 44 that contains the slot 45. Indentations are formed in the distal edge of the first section 140 and second section 150; these indentations form part of the side wall of the slot 45. The indentation in section 140 has a chamfer 46 to direct the needle 70 into the slot 45. The end cap 160 is placed against the distal edge of the first section 140 and the second section 150. An indentation in the end cap 160 forms the remainder of the side wall of the slot 45. The end cap 160 forms the distal end of long leg 44.

A shim 142 is placed between the first section 140 and the second section 150. The shim 142 is a flat piece of resilient material, such as metal. A receiving notch 152 in the second section 150 receives the shim 142 (see FIG. 6A). The receiving notch 152 contains a flat portion 154 and a sloped portion 156. The flat portion 154 is recessed into the second section 150 to a depth approximately equal to that of the thickness of the shim 142. The sloped portion 156 is distal to the flat portion 154, and the depth gradually increases to a depth somewhat greater than the shim 142 thickness at the distal edge of the second section 150. The receiving notch 152 is positioned in the second section 150 so that a portion of the shim 142 extends into the slot 45 when the shim 142 is placed within the receiving notch 152.

Figure 6A:
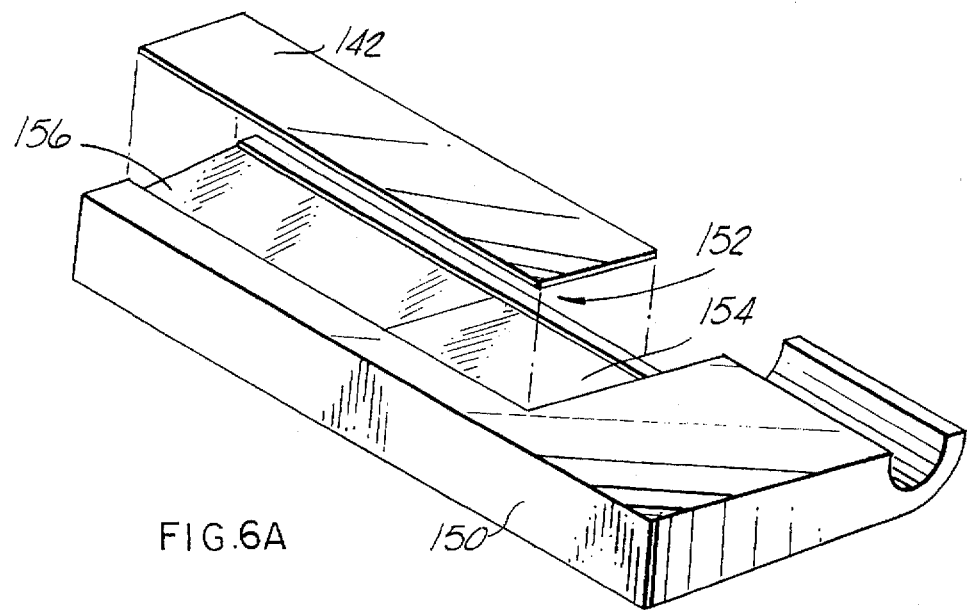
FIG. 6A is a perspective view of a portion of the needle guide of FIG. 6.
Figure 6B:
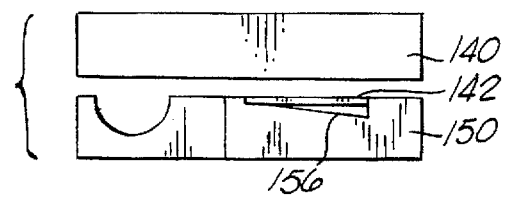
FIG. 6B is an end view of the needle guide of FIG. 6.
Figure 6C:
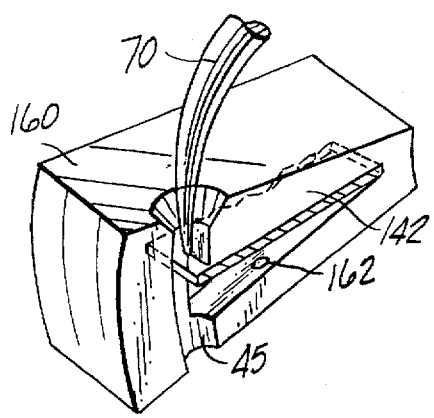
FIGS. 6C, 6D, and 6E show a portion of the needle guide of FIG. 6 as a needle passes through the needle guide.
Figure 6D:
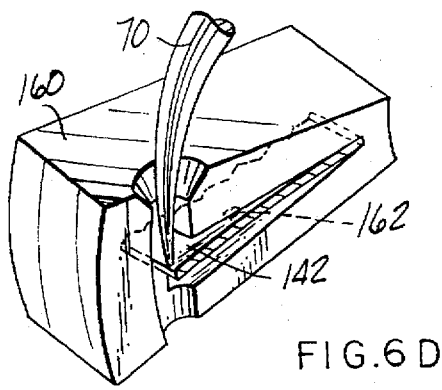
Figure 6E:
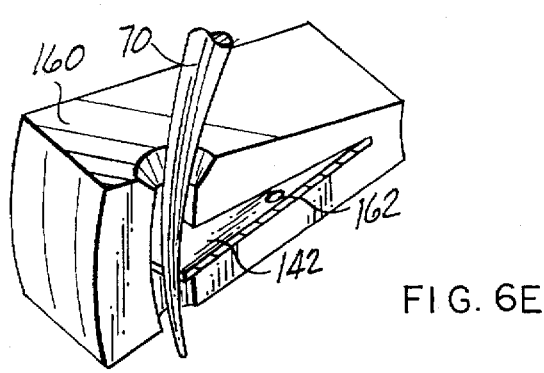

The surface of the first section 140 that abuts the second section 150 is essentially flat. When the first section 140 is connected to the second section 150, the shim 142 will also abut the first section 140 since the receiving slot flat section 154 is only the depth of the shim 142 thickness. As best illustrated in FIG. 6B, space is present between the sloping section 156 of the receiving notch 152 and the shim 142.

As seen in FIG. 6 and FIGS. 6C–6E, the end cap 160 contains a notch 162 that aligns with the receiving notch 152. When there is no force on the shim, the shim will fit into a portion of the notch 162 that is closer to the first section 140 than to the second section 150 (see FIG. 6C).

When the needle 70 is passed through the slot 45, the needle 70 will contact the shim 142, since the shim extends into the slot 45. Assume that the needle is passed from the first section 140 to the second section 150. Continued movement of the needle 70 will deflect the resilient shim 12 (see FIG. 6D). Eventually, a section of the shim 142 in the second section 150 will deflect into the sloped section 156 of the slot 152, and a corresponding section of the shim 142 in the end cap 160 will deflect from the side of the notch 162 closest to the first section 140 to the side of the notch 162 closest to the second section 150 (see FIG. 6E).

Once the sharp end 71 of the needle 70 has passed the shim 142, the motion of the needle 70 cannot be reversed. If the needle 70 motion were reversed, the shim 142 would revert to its unflexed position, i.e., adjacent to the first section 140. To do so, the shim 142 edge that extends into the slot 45 would have to travel in an arc from its position in the sloped portion 156 of the receiving notch 152 back to its initial position, in contact with the needle guide section 140. However, the needle 70 forms a close tolerance with the slot 45, so there is no room to allow shim 142 to travel in such an arc. Note that the forward motion of the needle 70, i.e., from the first needle section 140 to the second needle section 150, is unhindered, because the shim 142 is sufficiently flexed by its motion from its initial position to the sloped portion 156 of the receiving notch 152 that its edge does not sufficiently protrude into the slot 45 to impede the motion of the needle 70. Stated another way, the needle 70 can move in its initial direction because the needle 70 has already deflected the shim 142 out of the direct path of the needle 70. The needle 70 cannot reverse direction because that would require that the shim 142 bend in the opposite direction, and the tolerances of the needle 70, slot 45, and shim 142 are such that there is insufficient space for that to occur.

When the forward motion of the needle 70 is halted and the needle guide 40 is moved forward, the slot 45 will pull the needle 70 along instead of allowing the guide 40 to slide over the needle 70. If the guide 40 were to slide over the needle 70, the relative motion between the guide 40 and the needle 70 would be the same as if the guide 40 were held stationary and the needle 70 were attempted to be moved from the second section 140 to the first section 150.

The passing of the needle 70 from one guide 40, 50 to the other is an extension of passing the needle 70 through one guide. As the needle 70 is passed from the first guide 40 to the second guide 50, the needle 70 deforms a second shim (not shown) in the second needle guide 50, in exactly the same way as the first shim was deformed, as described above (see FIG. 6C). When the movement of the needle is stopped and the second guide 50 is moved in the same direction as the needle 70 initially was moved, the second guide 50 will pull the needle 70 along to prevent the needle 70 from moving through the second needle slot 55 in the reverse direction (see FIGS. 3B, 3C). The first needle guide 40 is held stationary at this time, and the needle 70 travels through the first needle guide 40 from the first section 140 to the second section 150.

The attachment between the first section 140 of the needle guide 40 and the second section 150 of the needle guide may be perfected by a variety of methods. A preferred method is simply to form the attachment with the screw 42 that tensions the guide 40 onto the tube. Similarly, the end cap 160 is preferably attached to the remainder of the needle guide 40 (either section 140 or 150) by a fastener such as a screw (not shown), although other methods, such as the use of adhesives, may also produce good results.

Figure 7:
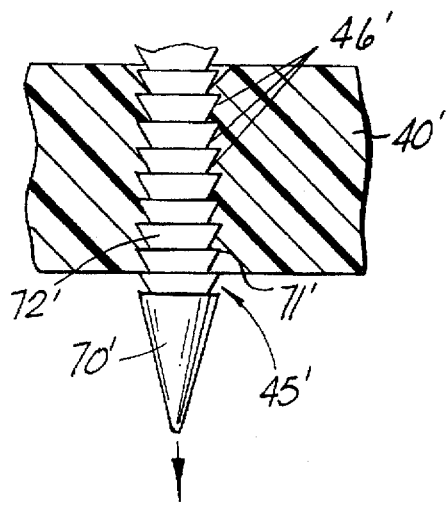
FIG. 7 shows an alternative embodiment of the one way slot of FIG. 6.

While the above described one way slots 45, 55 are preferred, it should be understood that other methods of achieving one way action are also possible and are alternate embodiments of the present invention. For instance, in an alternate needle guide 40', the needle 70' may have teeth 71' formed in its periphery which may slide through pawls 46' formed in the needle slot 45' in one direction, but would bind if the needle 70' were attempted to be slid in the opposite direction (see FIG. 7).

Figure 10:
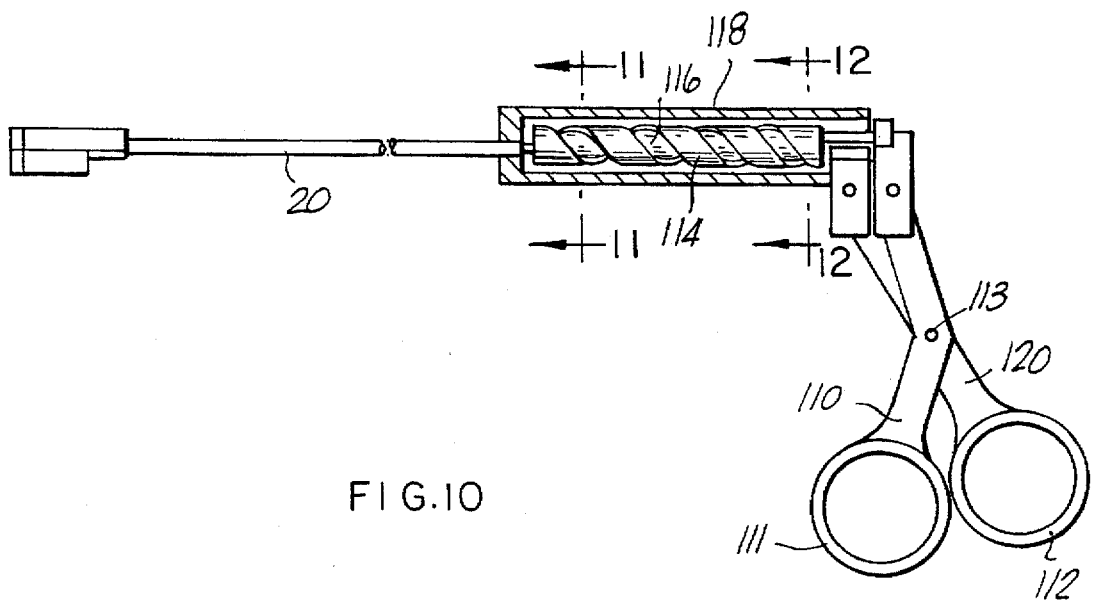
FIG. 10 shows a side elevation sectional view of FIG. 1, including a handle mechanism.
Figure 11:
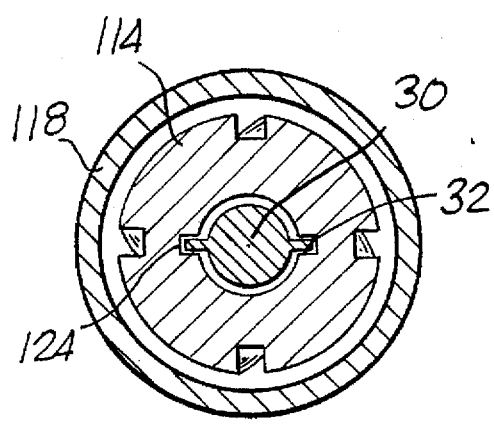
FIG. 11 shows a cross-section view of FIG. 10 taken along the line 11—11.

With reference to FIG. 10, the device 10 preferably includes a handle 100 that enables the rod 30 and the tube 20 to be relatively rotated. The handle 100 includes two lever arms 110, 120, both lever arms being terminated at one of their ends in a loop 111, 121 respectively, so that the handle 100 may be easily grasped by the operator of the device 10 by inserting a finger through each loop 111, 121. The lever arms 110, 120 are pivotally connected to each other at pivot point 113.

Figure 12:
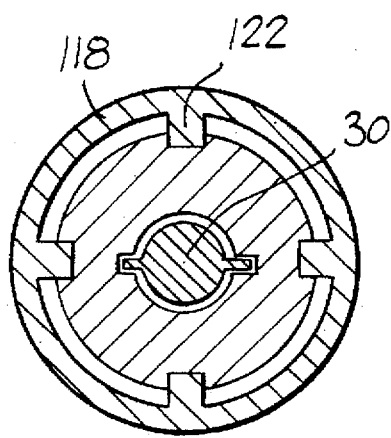
FIG. 12 shows a cross-section of FIG. 10 taken along the line 12—12.

Lever arm 110 is connected to a hollow screw 114, preferably having four independent threads 116. The screw 114 is aligned with the axis of the rod 30, and the proximal end of the screw 114 is attached to the rod 30, in a manner described below. Separating lever arm 110 from lever arm 120 longitudinally retracts the screw 114. The screw is at least partially encased by a handle body 118. Four pins 122 are spaced around the interior of the body 118, so that one pin fits within each of the four threads 116 (see FIG. 12). The longitudinal motion of the screw 114 causes the screw 114 to rotates the threads 116 mesh with the pins 122.

Figure 13:
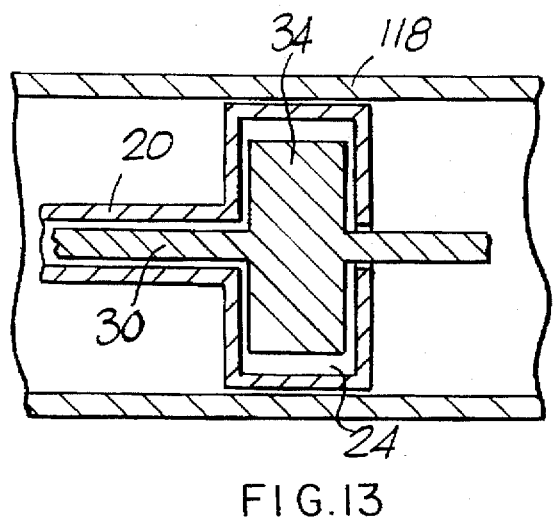
FIG. 13 is a sectional view of the proximal portion of the rod and tube depicted in FIG. 2.

The screw 114 may slide with the rod 30 longitudinally, but is rotationally fixed to the rod 30. This is preferably accomplished by two radial wings 32 rod that extend from the distal portion of the rod 30 that fit into two slots 124 formed into the interior portion of the screw 114. The rod 30 may move longitudinally in the screw 114, because the wings 32 may move longitudinally within the slots 124. However, rotation of the screw 114 will cause rotation of the rod 30, as the slots 124 grip the wings 32. The rod 30 is longitudinally connected to the tube 20, although the rod 30 and tube 20 may rotate with respect to each other. This may be accomplished by an annular ridge 34 on the rod 30 that fits into a groove 24 on the tube 20 (see FIG. 13). Note that since each lever arm 110, 120 may be controlled by a finger (or thumb) of the surgeon, the device 10 may be operated with only one hand. The tube 20 is rigidly connected to the handle body 118, so that the tube 20 may be rotated by rotating the handle body 118.

Figure 8:
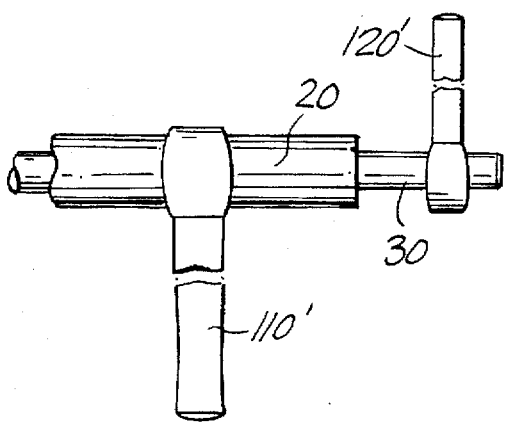
FIG. 8 shows one embodiment of the handle at the proximal end of the device of FIG. 1.

An alternate embodiment dispenses with the handle 100 (see FIG. 8). Instead, an arm 110' is firmly attached to the tube 20 and another arm 120' is firmly attached to the rod 30, with both arm 110', 120' axes transverse to the rod 30 and tube 20 axes. The surgeon may then rotate the arms 110', 120' to rotate the needle guides 40, 50. While this alternate embodiment is simpler and less expensive to manufacture than the preferred embodiment, it is not easily operated with one hand.

The device 10 may be inserted through an introducing tube (not pictured) to reach the operation site of a patient, as occurs in laparascopic surgery. The handle 100 would remain proximal to the introducing tube, so that it may be manipulated by the surgeon. The device 10 may be dimensioned to fit through an introducing tube of a desired diameter, depending upon the specific suturing needs of differing operations.

Figure 9:
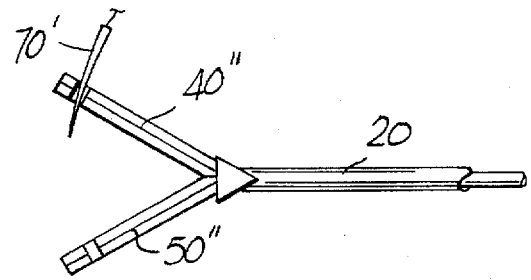
FIG. 9 shown an alternate embodiment of the needle guides of FIG. 1.

It should be appreciated that the above described embodiment and alternate versions thereof could be modified in many ways without materially affecting the performance of the invention. For example, the needle guides 40, 50 as above described contain three parts, and the shim 142. However, some of these parts could be combined together, although that may complicate the manufacturing process. As another example, the needle guides 40, 50 have been described as L shaped. The L shape effectively allows one section of a guide 40, 50 to be attached to the tube 20 or rod 30, and another section of the guide 40, 50 (containing the guide slots 45, 55) to project longitudinally and radially beyond the distal end of the tube 20 and rod 30. However, other shapes may accomplish the same purpose using the same principle. For example, needle guides 40", 50" could be straight arms that attach to the rod or the tube and extend distal and radially away from the distal end of the rod (see FIG. 9).

We claim:

1. A suturing apparatus for a needle having a sharp end and suture material attached to the needle opposite the sharp end, comprising:

a first needle guide and a second needle guide, each guide containing a directional slot having a first slot side and a second slot side, each guide slot having directional means for allowing the needle to pass through the slot from the first slot side to the second slot side opposite the first slot side and preventing the needle from passing through the slot from the second slot side to the first slot side;

the first and second needle guide slots being rotationally mounted in relation to one another, whereby rotating the guide slots passes the needle from the first needle guide slot to the second needle guide slot further rotating the guide slots passes the needle from the second guide to the first guide slot, the sharp end of the needle passing through each guide slot from the first slot side to the second slot side, the needle moving in a single direction.

2. The apparatus of claim 1, further comprising: a tube having a distal end and a proximal end, the first needle guide being mounted to the distal end of the tube; and a rod having a distal end and a proximal end, the rod being located partially within the tube and being rotatable therewithin, with the distal end of the rod extending past the distal end of the tube, the second needle guide being mounted to the distal end of the rod.

3. The apparatus of claim 2, wherein the needle slots of the first needle guide and the second needle guide are located distal to the rod and radially apart from the rod axis.

4. The apparatus of claim 3, wherein the first needle guide directional mean includes a shim, the shim being made of a resilient material, with a portion of the shim extending into the first needle guide slot.

5. The apparatus of claim 4, wherein the first needle guide contains a recessed portion to contain the shim, the recessed portion being wider than the thickness of the shim at the portion of the shim that extends into the first needle guide slot, and the recessed portion being approximately the thickness of the shim at a portion of the shim that does not extend into the first needle guide slot, so that the shim is at least partially displaced by the needle as the needle moves through the first needle guide slot.

6. The apparatus of claim 5, wherein the second needle guide slot has substantially the same structure as the first needle guide slot.

7. The apparatus of claim 6, further comprising a handle, the handle being attached to the proximal ends of the tube and the rod and including means for relatively rotating the rod and tube.

8. The apparatus of claim 7, wherein the handle comprises:

a first lever arm and a second lever arm, the lever arms being pivotally connected to one another;

a threaded screw having a distal end and a proximal end, the proximal end of the screw being attached to the second lever arm, and the distal end of the screw being attached to the rod;

a handle housing, with a protrusion adapted to fit into a thread of the threaded screw; and the handle housing at least partially contains the screw, pivoting the first and second lever arms moves the screw with respect to the handle housing in the direction of the screw axis, and the movement of the screw thread through the handle housing protrusion causes the screw to rotate with respect to the handle housing.

9. The apparatus of claim 8, wherein the rod contains a flange that extends radially away from the rod axis, and the screw contains a hollow section adapted to receive the rod section including the flange, so as to form a close tolerance therewith.

10. A method of suturing a surface comprising the steps of:

(a) placing a needle through a first needle guide, the needle having a sharp end and suture material attached to an opposite end, so that the sharp end of the needle projects ahead of the needle guide;

(b) positioning the first needle guide on one side of the surface to be sutured;

(c) positioning a second needle guide on the opposite side of the surface;

(d) forcing the needle through the surface and into the second needle guide, so that the sharp end of the needle extends through the second needle guide;

(e) repositioning the first and second needle guides;

(f) forcing the needle through the surface to be sutured so that the sharp end of the needle extends through the first needle guide;

wherein the above steps are performed such that the needle is moved in a single direction and wherein the first needle guide is attached to a tube and the second needle guide is attached to a rod fitted at least partially within the tube and is rotatable therewithin, and steps (d)–(f) are accomplished by relatively rotating the tube and the rod.

11. The method of claim 10, wherein the tube and rod can be relatively rotated by manipulating a handle operatively engaged with the tube and rod.

12. The method of claim 11, wherein the needle guides allow relative motion between the guides and the needle in only one direction, and step (e) causes the needle to be completely withdrawn from the first needle guide.

13. The method of claim 12, step (e) further comprising: repositioning the needle guides longitudinally with respect to the axis of the tube.

14. The method of claim 13, wherein step (e) is partially performed by pushing the handle longitudinally with respect to the tube axis.

* * * * *